(12) United States Patent
Uchiwa et al.

(10) Patent No.: US 7,763,263 B2
(45) Date of Patent: Jul. 27, 2010

(54) SKIN EXTERNAL AGENTS AND DRUGS

(75) Inventors: Hideyo Uchiwa, Odawara (JP); Sachiyo Hirotsu, Odawara (JP); Akinori Haratake, Odawara (JP); Takeshi Ikemoto, Minamiasigara (JP); Junichi Matsui, Odawara (JP); Shunsuke Yamazaki, Odawara (JP); Masaki Yoshida, Odawara (JP); Motoi Hayase, Odawara (JP)

(73) Assignee: Kao Corporation, Tokyo (JP)

( * ) Notice: Subject to any disclaimer, the term of this patent is extended or adjusted under 35 U.S.C. 154(b) by 1145 days.

(21) Appl. No.: 11/400,651

(22) Filed: Apr. 7, 2006

(65) Prior Publication Data

US 2006/0177408 A1    Aug. 10, 2006

Related U.S. Application Data

(62) Division of application No. 10/169,040, filed as application No. PCT/JP00/08942 on Dec. 15, 2000, now Pat. No. 7,037,489.

(30) Foreign Application Priority Data

Mar. 30, 2000  (JP) .............................. 2000/93152
Oct. 24, 2000   (JP) .............................. 2000/323637
Nov. 9, 2000    (JP) .............................. 2000/341577

(51) Int. Cl.
*A61K 31/74*   (2006.01)
*A61K 6/00*    (2006.01)

(52) U.S. Cl. .................... 424/401; 424/78.03; 424/477; 424/445; 514/547

(58) Field of Classification Search ................. 424/401, 424/78.03, 78.02
See application file for complete search history.

(56) References Cited

U.S. PATENT DOCUMENTS 5,451,667 A   9/1995  Speiser et al. ................. 536/71
5,837,728 A   11/1998 Purcell ....................... 514/529

FOREIGN PATENT DOCUMENTS

DE   2924042    2/1980
DE   2621214    11/1997
JP   04-018017  1/1992
JP   09-255622  9/1997

OTHER PUBLICATIONS

Eckloff, W. et al. "Sprayable polymer solution for bandaging wounds comprises copolymer of dialkoxyalkyl fumarate and vinyl ester", Feb. 14, 1980, Derwent Acc. No. 1980-13177C, abstract of DE 2924042 B.*
"The Risk of Sensibilization and Contact Urticaria . . . " Pharmacology and Treatment; Dermatology 1994; 188: 126-130; The Journal of Investigative Dermatology; vol. 111, No. 5, Nov. 1998.
"Treatment of Psoriasis With Fumaric Acid Esters . . . " British Journal of Dermatology 1998; 138:456-460.
"Treatment of Severe Psoriasis With Fumaric Acid Esters . . . " British Journal of Dermatology 1999; 141:424-426.
Arroyo et al. Revista de Plasticos Modernos, 1073, 26(208), 574-80.

* cited by examiner

*Primary Examiner*—Gina C Yu
(74) *Attorney, Agent, or Firm*—Birch, Stewart, Kolasch & Birch, LLP

(57) ABSTRACT

The present invention provides a method for enhancing epidermal permeability barrier function of the aged skin, which includes the step of externally administering to the aged skin an amount of a fumaric acid diester derivative expressed by the following general formula (1) as an active ingredient $$R^2O-(R^1O)_n-\overset{\overset{O}{\|}}{C}-\underset{H}{\overset{H}{\underset{|}{C}}}=\underset{\overset{\|}{O}}{\overset{}{\underset{C-(OR^1)_n-OR^3}{|}}} \quad (1)$$

wherein $R^1$ represents a $C_{1-4}$ alkylene group; $R^2$ and $R^3$ each represents a linear or branched $C_{1-8}$ alkyl group; and n is an integer of 2 to 5.

4 Claims, No Drawings

SKIN EXTERNAL AGENTS AND DRUGS

This application is a division of Ser. No. 10/169,040 filed on Jun. 21, 2002, now U.S. Pat. No. 7,037,489 which in turn is a 371 of International Application No. PCT/JP00/08942 filed Dec. 15, 2000, both of which are incorporated herein by reference.

FIELD OF THE INVENTION

The present invention relates to skin external agents such as cosmetics and medicines. Particularly, the present invention relates to an epidermal permeability barrier function-enhancing agent which enhances the epidermal permeability barrier function against environmental influences such as sunburn and quickly ameliorates damaged function of epidermal permeability barrier such as dry skin to maintain the skin in a dermatological and cosmetologically healthy state.

The present invention relates also to an amphiregulin expression inhibitor and an epidermal hyperproliferation inhibitor which are useful for therapy, prevention, and studies on various diseases involving excessive amphiregulin expression and dry skin.

Further, the present invention relates to an ameliorating agent for aged skin which prevents metabolic disruption and thinning of the skin due to aging and is effective in treatment of age spots. Still further, the present invention relates to an agent that is used together with retinoic acid or a derivative thereof in order to prevent side effects, such as dry skin, caused by retinoic acid or a derivative thereof.

DESCRIPTION OF THE PRIOR ART

All organisms including the human being are influenced by their external environment. However, higher animals such as mammal have an organ which minimizes the environmental influence on other important organs and systems for life. The organ is the skin that has, as its most important function, an epidermal permeability barrier function to prevent foreign substances from invading into the body and excessive vaporization of moisture from the interior of the body.

The epidermal permeability barrier function can temporarily disrupt due to diseases or exposure to organic solvents, surfactants or UV-rays, which disturbs the skin's internal environments. If this condition continues, such a risk may arise that pathological bacteria and harmful chemical substances may invade through the skin into the interior of the body. Accordingly, it is necessary to quickly restore the epidermal permeability barrier function. In addition, in the state of disruption in the epidermal permeability barrier function, the epidermis becomes dry and its surface is covered with scales, which leads to a cosmetologically undesirable look.

The epidermal permeability barrier function is formed and maintained by keratinocyte turnover and keratinization near the stratum corneum. Where the epidermal permeability barrier function disrupts, hyperproliferation of keratinocytes occurs and continuous hyperproliferation is considered to deminish normal keratinocyte turnover and keratinization, which delays the recovery of the barrier function.

Psoriasis is a disease with unknown causes, and is accompanied with hyperproliferation of keratinocytes and keratinization insufficiency. Drugs such as steroids and Cyclosporin A, immunosuppressive agent, are generally administered for its treatment. However, it is pointed out that these drugs are dangerous for routine or daily application. Therefore, a drug is desired which reduces and normalizes epidermal hyperproliferation more safely. Similarly, a safe and effective external agent is in demand for dermatological diseases such as atopic dermatitis accompanied with disruption of the epidermal permeability barrier function.

Appearance of the skin is largely influenced by the skin's overall metabolic ability and its conditions. For example, when the epidermal permeability barrier function is disrupted, the skin surface becomes dry and is covered with scales, which is an undesirable state. By hypometabolism with aging, change in skin tone caused by thinning of the epidermis, dullness, age spot, and wrinkles, lead to loss of beauty in appearance.

The appearance of a beautiful skin is maintained by active keratinocyte turnover and normal keratinization near the stratum corneum. When the keratinocyte turnover is lowered, keratinization may not proceed smoothly, resulting in dry skin. Lowered turnover due to aging results in dullness in the skin or age spots caused by accumulated melanin. The epidermal turnover is considered to depend on a cellular mitosis rate in the basal layer, and a decreased mitosis rate due to aging results in thinner epidermis and wrinkles as well.

The keratinocyte turnover is considered to be controlled by the expression of epidermal growth factors such as amphiregulin, heparin-binding EGF-like growth factor (HB-EGF), and TGF-α. In particular, HB-EGF expressing near the basal layer is considered to be the greatest contributing factor and, therefore, the epidermal turnover is up-regulated by inducing the HB-EGF expression [Journal of Investigative Dermatology (1998), Vol. 111, pp. 715 to 721].

Retinoic acid is known as a very effective external agent and is also known to induce HB-EGF expression. On the other hand, retinoic acid has side effects such as dry skin and temporary darkening, so that, if it is used as a skin topical agent, physicians must monitor the patients very carefully. Therefore, patients who need routine prevention and treatments desire the development of safer drugs and a means to prevent such side effects.

It is known that the expression of amphiregulin does not occur in the skin showing normal turnover, but is restricted in the epidermis exhibiting hyperproliferation or proliferation in cultured keratinocytes. Consequently, it is believed that the epidermal hyperproliferation can be inhibited specifically and effectively and, accordingly, functions of the skin are normalized by inhibiting the expression of amphiregulin. The expression of amphiregulin is involved not only in the hyperproliferation of the skin, but also in the process of development of skin cancer according to a report. However, any substance is not yet known which specifically inhibits the expression of amphiregulin. Therefore, also for the purpose of research progress, the development of a drug which inhibits the expression of amphiregulin is strongly desired.

The inventors found that dimethyl fumarate and diethyl fumarate are effective for ameliorating the epidermal permeability barrier function (Japanese Patent Application Laid-Open No. 12-178116/2000). In addition, it is known that fumaric acid and fumaric acid esters have a sebum secretion-promoting function (Japanese Patent Application Laid-Open No. 4-18017/1992), and fumaric esters are orally administrated for the treatment of psoriasis (British Journal of Dermatology 1998:138:456-460, 1999:141:424-429). However, it is also known that, when they are used externally, perilesional skin irritation, mascular papular rashes, and urticarial reactions are caused and there is a risk of causing sensitization and contact urticaria (Dermatology 1994:188:126-130).

DISCLOSURE OF THE INVENTION

The purpose of the present invention is to provide an epidermal barrier function-enhancing agent and a composition for skin external application which are very safe, quickly ameliorate the epidermal permeability barrier function disruption, and have excellent effects on maintaining the skin in a cosmetologically healthy state; a HB-EGF expression-inducing agent to accelerate epidermal turnover; an amphiregulin expression inhibitor to deminish epidermal hyperproliferation; an agent to be used together with retinoic acid or a derivative thereof to prevent dry skin caused by retinoic acid or a derivative thereof; and an ameliorating agent for aged skin which ameliorates hypometabolism and thinning of the skin due to aging.

To attain the aforementioned purposes, the inventors earnestly have investigated effects and safety on skin of various kinds of fumaric acid diester derivatives, and have found that the fumaric acid diester derivatives expressed by the following general formula (1) are safe to skin (i.e., not showing sensitization) and have an excellent epidermal permeability barrier-function enhancing function. The inventors have also found that a skin external agent composition containing this derivative has excellent effects of ameliorating the epidermal permeability barrier function; maintaining the skin in a dermatologically and cosmetologically healthy state; inducing the expression of HB-EGF; inhibiting the expression of amphiregulin; preventing skin thinning due to aging; and preventing dry skin caused by retinoic acid.

The present invention provides an epidermal permeability barrier function-enhancing agent, an amphiregulin expression inhibitor, an epidermal hyperproliferation inhibitor, a heparin-binding epidermal growth factor-like growth factor (HB-EGF) expression inducing agent, an ameliorating agent for aged skin, an agent to be used together with retinoic acid or a derivative thereof, an agent to prevent dry skin caused by retinoic acid, and a skin external agent composition, which all comprises fumaric acid diester derivatives expressed by the following general formula (1)

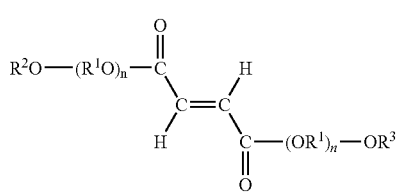

(1)

wherein $R^1$ represents a $C_{1-4}$ alkylene group; $R^2$ and $R^3$ each represents a linear or branched $C_{1-8}$ alkyl group; and n is an integer of 2 to 5. The present invention also provides a skin external agent composition comprising the aforesaid fumaric acid diester derivatives, and retinoic acid or a derivative thereof.

DESCRIPTION OF THE PREFERRED EMBODIMENTS

The embodiments of the present invention will be described below in detail.

Examples of the fumaric acid diester derivatives expressed by the aforementioned general formula (1) used in the present invention include bis(diethylene glycol monoethyl ether)fumarate expressed by the following general formula (2):

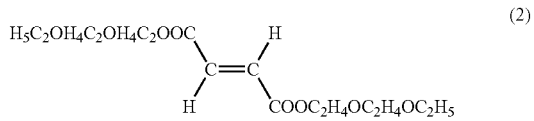

(2)

such as bis(triethylene glycol monoethyl ether)fumarate, bis(diethylene glycol monomethyl ether)fumarate, bis(triethylene glycol monomethyl ether)fumarate, bis(diethylene glycol monobutyl ether)fumarate, and bis(dipropylene glycol monoethyl ether)fumarate. These substances are all known. Those with n=2 or 3 are particularly desirable from the viewpoint of lipophilic/hydrophilic balance.

The fumaric acid diester derivatives expressed by the aforementioned general formula (1) used in the present invention can be manufactured by a known method described in, e.g., Japanese Patent Application Laid-Open No. 9-255622/1987.

In the aforementioned general formula (1), to represent the fumaric acid diester derivatives used in the present invention, the $C_{1-4}$ alkylene groups, $R^1$, can be identical with or different from each other. When different kinds of the alkylene groups, such as $C_2H_4$ and $C_3H_8$, are present together, they may be bound randomly or in block-wise. The $C_{1-8}$ linear or branched alkyl groups for $R^2$ and $R^3$ can be identical with or different from each other.

A preferable amount of the fumaric acid diester derivative to be blended in the present skin external agent composition ranges from 0.001 to 15.0 mass % (hereinafter simply expressed by "%") and more preferably from 0.1 to 10.0% relative to a total amount of the skin external agent composition. If the amount is less than 0.001%, the intended effects of the present invention may not be attained sufficiently. On the other hand, if the amount exceeds 15.0%, there may be no proportional increase in the effects, which may not be desirable sometimes.

Conventional external bases and other pharmaceutical active components can be added to the present epidermal permeability barrier function-enhancing agent, the amphiregulin expression inhibitor, the epidermal hyperproliferation inhibitor, the heparin-binding epidermal growth factor-like growth factor (HB-EGF) expression-inducing agent, the aged skin ameliorating agent, the agent to be used together with retinoic acid or a derivative thereof, and the agent to prevent dry skin caused by retinoic acid or a derivative thereof. The external bases include oily bases, water-in-oil and oil-in-water emulsion type bases, and water-based ones. Nonrestrictive examples of the oily bases are vegetable oils, animal oils, synthetic oils, fatty acids, and natural or synthetic glycerides. As the pharmaceutical components, any ones can be used appropriately as desired, for example, analgetic and anti-inflammatory agents, bactericidal sterilization agents, astringents, skin emollients, hormones and vitamins. In addition, the following compounds can be blended in any combinations: humectants, UV-ray absorbents, alcohols, chelating agents, pH modifiers, antiseptics, thickening agents, pigments, perfumes and plant extracts.

The fumaric acid diester derivatives expressed by the general formula (1) are soluble in water, so that they are advantageously formulated.

The agent to be used together with retinoic acid or a derivative thereof in the present invention can be administrated externally, orally or by injection when retinoic acid or its derivative is administrated. External administration is desirable. In a skin external agent composition as one of the forms of administration, the fumaric acid diester derivatives expressed by the aforementioned general formula (1) can be formulated together with retinoic acid or a derivative thereof.

A retinoic acid derivative having a physiological activity equivalent to that of retinoic acid can be used besides retinoic acid.

When retinoic acid or derivative thereof is used together with the fumaric acid diester derivatives expressed by the aforementioned general formula (1), an amount of retinoic acid or derivative thereof to be used is not particularly limited, but a preferable amount ranges from 0.001 to 1 mass % and more preferably from 0.01 to 0.5 mass %.

Moreover, the aforesaid agents or drugs can be incorporated in usual cosmetics and bath agents as well as in skincare cosmetics. They can be in any dosage form such as lotions, milky lotions, creams, packs, powder and granules. They can be applied to any part of the human skin, including scalp. When applied on the scalp, anti-dandruff and hair tonic effects are expected.

The skin external agent compositions as described above include medicines for diseases such as psoriasis and atopic dermatitis, quasi-drugs and cosmetics. The cosmetics include general cosmetics such as skincare cosmetics, makeup cosmetics, cosmetic bases and hair care cosmetics as well as bath agents, among which the skincare cosmetics are most desirable since they take the full advantage of the present invention. They can be in any dosage form such as lotions, milky lotions, creams, packs, powder, granules, gels and ointments.

In addition to the substances mentioned above, vehicles, surfactants and antioxidants allowed to be used in medicines, quasi-drugs or cosmetics can be blended in the present drugs or the skin external agent compositions in such an amount that the purpose of the present invention is achieved.

EXAMPLES

The present invention will be explained with reference to the following Tests, Examples and Comparative Examples.

Test 1

Epidermal Permeability Barrier Function Amelioration Test

An effect of improving epidermal permeability barrier function by applying the agents on the skin of which epidermal permeability barrier function has been disrupted was evaluated by the following test method.

1. Experimental Animals Used

Male hairless mice (Hos: Hr-1) of 10 weeks old at the beginning of the test were used with each 5 mice per group.

2. Measurement of the Epidermal Permeability Barrier State 2-1. Measurement Device and Conditions Transepidermal water loss (TEWL) was measured as follows using a continuous perspiration measurement device, Hydrograph AMU-100 (ex K & S Co., Ltd.). A 1 $cm^2$ capsule was closely attached to the skin and nitrogen gas was led into the capsule in a rate of 300 mL/min. The amount of water vapor in the nitrogen gas was measured before the gas was fed to the capsule and after it was recovered from the capsule. From a difference between the amounts, the amount of water in mg_vaporized from 1 $cm^2$ area of the skin per minute, TEWL, was calculated.

2-2. Samples and the Experimental Method

The samples were prepared by mixing the compounds indicated in Table 1 below, e.g., bis(diethylene glycol monoethyl ether)fumarate, with a 50% aqueous ethanol solution (base). The TEWL of the hairless mouse dorsal skin was first measured at the beginning of the test. Subsequently, 0.05 mL of each sample was applied on an area of approximately 2.5 cm diameter in the dorsal skin of the hairless mice once a day from Monday to Friday (pre-application). Then, on the third day from the last day of the pre-application, the skin was irradiated once with ultraviolet B ray (UVB) at a dose of 0.15 $J/cm^2$. Each sample was applied immediately after the UVB irradiation until the $3^{rd}$ day from the irradiation in the same amount and at the same frequency as in the pre-application. The TEWL was measured on the $3^{rd}$ and $4^{th}$ days after the irradiation. TEWL change rates (=TEWL value on the $3^{rd}$ or $4^{th}$ day after the irradiation/TEWL value at the beginning of the test) were calculated, which show changes in TEWL relative to the initial TEWL due to the exposure to UVB, and the mean values thereof were compared between the control group and each sample group.

2-3. A Method of Assessment of the Effects

TEWL changes with the degree of disruption of the epidermal permeability barrier function. A higher value of TEWL change rate implies a greater degree of disruption of the epidermal permeability barrier function. In the case of the application of the base alone, disruption in the epidermal permeability barrier function by UVB was similar to that in the case of non-application. Therefore, a group showing a lower TEWL change rate than that of the control group, where the base alone was applied and thus showed the natural state of the disruption in the epidermal permeability barrier function, was assessed as available in the epidermal permeability barrier function amelioration.

The TEWL change rates in the hairless mice after the application of the samples are as shown in Table 1.

TABLE 1

| Compounds | Concentrations, % | TEWL change rate $3^{rd}$ day | $4^{th}$ day |
|---|---|---|---|
| Bis (diethylene glycol monoethyl ether) fumarate | 1 | 3.25 | 2.49 |
| — | 0 | 7.98 | 7.27 |
| Diphenylethyl fumarate | 1 | 7.82 | 6.57 |
| Dimethyl fumarate | 1 | 3.24 | 2.50 |
| | | | Mean values |

As is seen from the results of this test, bis(diethylene glycol monoethyl ether)fumarate which is a fumaric acid diester derivative according to the present invention clearly reduces disruption in the epidermal permeability barrier function by UVB and ameliorates epidermal permeability barrier function, compared to the base alone and diphenylethyl fumarate, and its epidermal permeability barrier function amelioration effects is as great as that of dimethyl fumarate which has sensitizing potential.

Next, a similar test was carried out using bis(diethylene glycol monoethyl ether)fumarate in various concentrations as described in Table 2 below.

TABLE 2

| Compounds | Concentrations, % | TEWL change rate | |
| --- | --- | --- | --- |
| | | 3rd day | 4th day |
| Bis (diethylene glycol monoethyl ether) fumarate | 0.001 | 7.01 | 7.31 |
| Bis (diethylene glycol monoethyl ether) fumarate | 0.01 | 6.46 | 6.84 |
| Bis (diethylene glycol monoethyl ether) fumarate | 0.1 | 3.79 | 5.21 |
| Bis (diethylene glycol monoethyl ether) fumarate | 1 | 3.62 | 4.33 |
| — | 0 | 8.56 | 8.11 |
| | | | Mean values |

Test 2

Safety (Sensitization) Test

Safety (sensitization) was evaluated by a maximization test. An area of 4×6 cm² of skin on the scapula of a Hartley strain guinea pig (female) weighing 350 to 400 g was shaved and given intradermal injections with each three injections in two lines according to the following procedures:

(1) each 0.05 mL of Freunds' Complete Adjuvant (hereinafter simply called FCA) was intradermally injected at each one spot in the right and left sites
(2) each 0.05 mL of a 3% fumaric acid diester derivative solution in ethanol of as a test sample was intradermally injected at another each one spot in the right and left sites.
(3) to a 6% fumaric acid diester derivative solution in FCA as a test sample, the same amount of sterilized water was added and resultant emulsified solution was intradermally injected at a right side and a left side sites in an amount of 0.05 mL.

At one week after the aforementioned procedures, the skin of the same sites was shaved and 10% of sodium lauryl sulfate in vaseline was applied to cause light inflammation. After 24 hours from the application, 0.2 mL of a 3% fumaric diester derivative solution in ethanol as a test sample, which was applied on a piece of gauze, was patched close on the same sites for 48 hours. On the 21st day after the intradermal injection, the abdominal area was shaved, to which a solution of a fumaric acid diester derivative in ethanol as a test sample, which was applied in a piece of gauze, was patched close for 24 hours. The symptoms in the skin were visually examined according to the following criteria after 48 hours.

| Symptoms | Rating |
| --- | --- |
| No reaction | 0 |
| Scattered mild redness | 1 |
| Moderate and diffuse redness | 2 |
| intense redness and swelling | 3 |

2. Test Results

The sensitization test results with various fumaric acid diester derivatives after 48 hours are shown below. As seen from the test results, bis(diethylene glycol monoethyl ether) fumarate, which is a fumaric acid diester of the present invention, was confirmed to have no sensitizing potential. However, bis(ethylene glycol monomethyl ether)fumarate which has the general formula (1) with n=1 was found to have sensitizating potential as diethyl fumarate did.

| Test samples | Positivity |
| --- | --- |
| Diethyl fumarate | 90% |
| Bis (ethylene glycol monomethyl ether) fumarate | 90% |
| Bis (diethylene glycol monoethyl ether) fumarate | 0% |

Test 3

Human Dry Skin Amelioration Test

A skin lotion having the composition described below was prepared by the formulation method described below. The sample lotion was applied on skin at an inside of an upper arm of 10 healthy subjects (males of 25 to 52 years old) and tested for human dry skin amelioration (epidermal permeability barrier function recovery test). As a control, one having the same composition except for bis(diethylene glycol monoethyl ether)fumarate was used.

| Skin lotion composition | Amount, % |
| --- | --- |
| Component (A) | |
| Olive oil | 10.0 |
| Isopropyl myristate | 1.0 |
| Polyoxyethylene (15) nonylphenyl ether | 0.5 |
| Propylene glycol | 1.0 |
| Glycerin | 2.0 |
| Component (B) | |
| Methylparaben | 0.1 |
| Ethanol | 7.0 |
| Bis (diethylene glycol monoethyl ether) fumarate | 1.0 |
| Purified water | Balance |

Preparation Method

Components (A) and (B) were separately dissolved uniformly, and then were combined to disperse with stirring. The mixture was filled in a container. The contents were shaken to effect uniform dispersion before each use.

Each sample was applied to the test site (2 cm×2 cm for each sample) in an amount of 0.1 mL once a day after bathing, which was continued for 2 months (61 days). On the 62nd day from the beginning of the application, the skin surface was wiped with acetone to attain 0.15 mg/cm²/min of TEWL, indicating an induced state of dry skin. Subsequently, the sample was applied again in the same way as described above. Along with investigating how much the epidermal permeability barrier function recovers, and also the skin surface status and the presence of side effects such as rashes and itching were examined.

The skin lotion with the aforementioned composition according to the present invention clearly demonstrated the dry skin amelioration effect compared to the control. Further, no skin abnormalities such as rashes and dryness were observed.

Test Example 4

Test of Measuring an HB-EGF Expression Rate

The HB-EGF expression rates were investigated by the following test methods where the compounds of the present invention were applied on the keratinocytes.

1. Keratinocytes Used in the Test

Cultured keratinocytes of human epidermis origin, commercially available from Kurabo Corporation, were used.

2. Measurement of HB-EGF Expression in the Keratinocytes (1) Experimental Method Keratinocyte sususpension was adjusted to a concentration of $400\times10^4$ units/mL on an MCDB153 culture medium supplemented with BPE (bovine pituitary extract), insulin, ethanolamine, phosphoethanolamine, and hydrocortisone as growth promotors. Four milliliters of the cell suspension was inoculated to a 60 mm plate (ex Falcon Corporation). Under an atmosphere of 95% (v/v) air and 5% (v/v) carbon dioxide gas, a confluent state was achieved by static culturing at 37° C. for 3 days, while refreshing the culture media every other day.

After removing the culture medium supernatant by suction, the culture medium was replaced with an MCDB 153 culture medium (containing insulin) to which dimethyl fumarate had been added at a final concentration of 50 μmol/L or bis(diethylene glycol monoethyl ether)fumarate in 300 μmol/L. This plate was subjected to static culturing at 37° C. for 24 hours under an atmosphere consisting of 95% (v/v) air and 5% (v/v) carbon dioxide gas. Using a QIAGEN™ RNA kit, whole mRNA was extracted. Each amount of HB-EGF mRNA and G3PDH mRNA per total mRNA was determined by Northern blotting. The amount of each mRNA per total in the absence of the fumarate was measured as the control. The amount of mRNA in the presence of the fumarate was expressed in % relative to those of the control.

(2) Results

The relative amounts of mRNA for HB-EGF and G3PDH in the presence of each sample are as shown below.

| Compounds added | Amount of mRNA, % relative to the control | |
|---|---|---|
| | HB-EGF | G3PDH |
| Bis(diethylene glycol monoethyl ether) fumarate | 380% | 98% |
| Dimethyl fumarate | 470% | 105% |

As can be seen from the above-mentioned results, bis(diethylene glycol monoethyl ether)fumarate induced the expression of HB-EGF as strongly as dimethyl fumarate which has sensitizing potential.

Test Example 5

Test on Capability of Inhibiting Reduction in Epidermis Thickness

The following test method was used in order to investigate inhibition of reduction in the epidermis thickness when the compound of the present invention was applied on aged skin.

1. Experimental Animals Used in the Test

Experimental animals used included 2 groups of aged hairless mice of 33 weeks old at the beginning of the test with each 5 mice per group, and one group of 5 hairless mice of 9 weeks old at the beginning of the test.

2. Measurement of the Epidermis Thickness (1) Samples and the Experimental Method A sample was prepared by adding bis(diethylene glycol monoethyl ether)fumarate to a 50% ethanol aqueous solution (base) at a concentration of 0.5%. This sample was applied in an amount of 0.05 mL on the dorsal skin of hairless mice (in a diameter of approximately 2.5 cm) once a day for consecutive 5 days per week followed by 2 days interval. This schedule was repeated for 4 weeks. Subsequently, a portion of the skin was sampled and a frozen section was prepared. The thickness of the epidermis was measured by microscopic observation. The mean values of the epidermis thicknesses in hairless mice after the application of the fumarate are shown below.

| Compound (Amount added) | Mean values of the epidermis thickness, μm |
|---|---|
| (33 weeks old hairless mice) | 20.96 |
| Bis (diethylene glycol monoethyl ether) fumarate (0.5%) | 17.24 |
| Untreated | |
| (9 weeks old hairless mice) | 28.88 |
| Untreated | |

The results of this test indicates that thinning of the epidermis due to aging was clearly inhibited by the addition of bis (diethylene glycol monoethyl ether)fumarate compared to the non-treatment.

Test Example 6

Test of Inhibition of the Expression of Amphiregulin

The amount of expression of amphiregulin in the keratinocytes was determined by the following test method.

1. Keratinocytes Used in the Test

Cultured keratinocytes of human epidermis origin (ex Kurabo Corporation) were used.

2. Measurement of Amphiregulin Expression in the Keratinocytes (1) Experimental Method Keratinocyte suspension was adjusted to a concentration of $150\times10^4$ units/mL in an MCDB153 culture medium supplemented with BPE (bovine pituitary extract), insulin, ethanolamine, phosphoethanolamine, and hydrocortisone as growth promotors. Four milliliters of the cell suspension was inoculated to a 60 mm plate (ex Falcon Corporation). Under an atmosphere of 95% (v/v) air and 5% (v/v) carbon dioxide gas, a confluent state was achieved by static culturing at 37° C. for 1 day.

After removing the culture medium supernatant by suction, the culture medium was replaced with an MCDB 153 culture medium (containing insulin) to which bis(diethylene glycol monoethyl ether)fumarate had been added in a final concentration of 300 mol/L or dimethyl fumarate in 70 μmol/L. This plate was subjected to static culturing at 37° C. for 24 hours under an atmosphere consisting of 95% (v/v) air and 5% (v/v) carbon dioxide gas. Using a QIAGEN™ RNA kit, whole mRNA was extracted. Each amount of amphiregulin and G3PDH mRNA per total mRNA was determined by Northern blotting. The amount of each mRNA per total in the absence of the fumarate was measured as the control. The amount of mRNA in the presence of the fumarate was expressed in % relative to those of the control.

(2) Results

The relative amounts of amphiregulin mRNA and G3PDH mRNA in the presence of each sample are as shown below.

| Agents added | Amount of mRNA, % relative to the control | |
|---|---|---|
| | Amphiregulin | G3PDH |
| Example 1. Bis (diethylene glycol monoethyl ether) fumarate | 8% | 102% |
| Comparative Example 1 Dimethyl fumarate | 39% | 98% |

The fumaric acid diester derivative of the present invention was found to inhibit the amphiregulin expression as strongly as dimethyl fumarate having sensitizing potential does. Since there was no difference in the amount of G3PDH mRNA between the control and Example 1, the mRNA expression inhibition action by the fumarate diester derivative was found to be specific to amphiregulin.

Test Example 7

Test of Inhibition of Amphiregulin Expression when Used Together with Retinoic Acid The amount of amphireglurin expression in the presence of retinoic acid in the keratinocytes was determined by the following method.

1. Keratinocytes Used in the Present Test

Cultured keratinocytes of human epidermis origin (ex Kurabo Corporation) were used.

2. Measurement of Amphireglurin Expression in the Keratinocytes (1) Experimental Method Keratinocyte suspensions was adjusted to a concentration of $400 \times 10^4$ units/mL in an MCDB153 culture medium supplemented with BPE (bovine pituitary extract), insulin, ethanolamine, phosphoethanolamine, and hydrocortisone as growth promotors. Four milliliters of the cell suspension was inoculated to a 60 mm plate (ex Falcon Corporation). Under an atmosphere of 95% (v/v) air and 5% (v/v) carbon dioxide gas, a confluent state was achieved by static culturing at 37° C. for 3 days, while refreshing the culture every other day.

After removing the culture medium supernatant by suction, the culture medium was replaced with an MCDB 153 culture medium (containing insulin) to which bis(diethylene glycol monoethyl ether)fumarate at a final concentration of 300 μmol/L or dimethyl fumarate at 70 μmol/L, and optionally retinoic acid at 1 μmol/L had been added. This plate was subjected to static culturing at 37° C. for 24 hours under an atmosphere consisting of 95% (v/v) air and 5% (v/v) carbon dioxide gas. Using a QIAGEN™ RNA kit, whole mRNA was extracted. Each amount of amphiregulin mRNA and G3PDH mRNA per total mRNA was determined by Northern blotting. The amount of each mRNA per total in rhe absence of the fumarate was measured as the control. The amount of mRNA in the presence of the fumarate was expressed in % relative to those of the control.

(2) Results

The relative amounts of amphiregulin mRNA and G3PDH mRNA after the addition of each sample are as shown below.

| Agents added | Amount of mRNA, % relative to the control | |
|---|---|---|
| | Amphiregulin | G3PDH |
| Example 2. Bis (diethylene glycol monoethyl ether) fumarate + retinoic acid | 70% | 102% |
| Comparative Example 2. Dimethyl fumarate + retinoic acid | 120% | 98% |
| Comparative Example 3. Retinoic acid alone | 300% | 105% |

As seen in Comparative Example 3, amphiregulin was strongly induced by the addition of retinoic acid and the induced amphiregulin is considered to be closely involved in formation of dry skin caused by retinoic acid. Example 2 reveales that the fumaric acid diester derivatives of the present invention more strongly inhibit the expression of amphiregulin induced by the addition of retinoic acid than dimethyl fumarate having sensitizing potential does. Since the amount of mRNA for G3PDH as the control in Example 2 agreed those in the Comparative Examples within an experimental error, the function of the fumaric acid diester derivative to inhibit the expression of mRNA was found to be specific to amphiregulin.

Test Example 8

Test of Inhibition of Dry Skin

The effect of inhibiting dry skin was investigated by the following test method in which the present fumarate was applied to the dry skin induced by retinoic acid.

1. Experimental Animals Used in the Test

Hairless mice of 10 weeks old at the beginning of the test were used with five mice per group.

2. Measurement of TEWL

A sample was prepared by adding dimethyl fumarate or bis(diethylene glycol monoethyl ether)fumarate to a 50% ethanol aqueous solution (base) in a concentration of 0.5%. This sample was applied in an amount of 0.05 mL to the dorsal skin of hairless mice (in a diameter of approximately 2.5 cm) once a day for consecutive 5 days (pre-application). Subsequently, 0.05 mL of a 0.05% retinoic acid solution in 50% ethanol aqueous solution was applied once a day for 4 days. During these 4 days, retinoic acid was applied in the morning, and, some hours later in the afternoon, the sample was applied. The TEWL values were measured by a Hydrograph AMU-100 (ex K & S Corp.) after completion of the application. In Comparative Example 5, a control sample comprising the base alone was used instead of the sample. In Comparative Example 6, the base was always applied.

The TEWL values after the application of the samples are as shown below.

| Group | Components | Mean value of TEWL, mg/cm$^2$/min. |
|---|---|---|
| Example 3 | Bis (diethylene glycol monoethyl ether) fumarate | 0.055 |
| Comparative Example 4 | Dimethyl fumarate | 0.063 |
| Comparative Example 5 | Retinoic acid, and no fumarate | 0.110 |
| Comparative Example 6 | Always the base only | 0.012 |

As seen above, increase in TEWL due to the application of retinoic acid was observed in Comparative Example 5 compared with Comparative Example 6 where the base alone was applied. In Example 3, because of the addition of the fumaric acid diester derivative of the present invention, apparently smaller increase in TEWL than in Comparative Example 5 was observed, which indicates amelioration of dry skin induced by retinoic acid. The TEWL value in Example 3 was almost equal to that in Comparative Example 4 where dimethyl fumarate having sensitizing potential was used.

Test Example 9

Test of Depression of UV-induced Epidermal Hyperproliferation

The inhibition of epidermal hyperproliferation was investigated by the following test method in which the present fumarate was applied to the skin where epidermal hyperproliferation had been induced by UV irradiation 1. Experimental Animals Used in this Test Example
   Hairless mice of 10 weeks old at the beginning of the test were used with 5 mice per group.
2. Measurement of Epidermis Thickness (1) Samples and Experimental Method
   Samples were prepared by adding dimethyl fumarate or bis(diethylene glycol monoethyl ether)fumarate to a 50% ethanol aqueous solution (base) at a concentration of 0.5%. Initially, this sample was applied in an amount of 0.05 mL to the dorsal skin of the hairless mice (in a diameter of approximately 2.5 cm) once a day and 5 times per week for 4 weeks (pre-application). Subsequently on the 3$^{rd}$ day from the last application of the pre-application, the skin was irradiated with a UVB ray once at a dose of 0.15 J/cm$^2$. The animals were slaughtered on the 4$^{th}$ day after the irradiation and skin section were made. From the section, tissue section samples were prepared by HE staining. The samples prepared were photographed using an light microscope. In the microscopic photographs, the thickness of the epidermis was measured. Using the epidermis thickness at the beginning of the test as a standard, the mean values were compared between the control group and the treated groups.

The mean values of thickness of the epidermis after the application of each sample are as shown below.

| Agents (Amount added) | Thickness of the epidermis (μm) |
|---|---|
| Bis (diethylene glycol monoethyl ether) fumarate (0.5%) | 61.6 |
| Dimethyl fumarate (0.5%) | 40.4 |
| 50% ethanol aqueous solution (base) | 103.9 |
| No application | 127.2 |

The results of the test show that the addition of fumaric acid diester derivatives inhibited epidermal hyperproliferation as shown in the reduced epidermal thickening by UVB, compared with the group treated with a base alone or the non-application group.

Application Example 1

Skin Cream

A skin cream was prepared by mixing the fumaric acid diester derivative according to the following composition.

(1) Composition

| Ingredients | Mixing ratio (mass %) |
|---|---|
| (Component A) | |
| Beeswax | 2.0 |
| Stearic acid | 5.0 |
| Stearyl alcohol | 5.0 |
| Hydrogenated lanolin | 2.0 |
| Squalene | 20.0 |
| Sorbitan monostearate | 3.0 |
| Polyoxyethylene (20) sorbitan monostearate | 3.0 |
| Propylene glycol | 5.0 |
| (Component B) | |
| Methylparaben | 0.2 |
| Purified water | Balance to the total of 100 |
| (Component C) | |
| Bis (diethylene glycol monoethyl ether) fumarate | 10.0 |

(2) Preparation Method
   Bis(diethylene glycol monoethyl ether)fumarate as Component C was added to Component B. After dissolving Components A and B separately by heating them to 80° C., both components were combined and then cooled to 30° C. while stirring to make a skin cream.

Application Example 2

Skin Lotion

A skin lotion was prepared by mixing the fumaric acid diester derivative according to the following composition.

| Ingredients | Mixing ratio (mass %) |
|---|---|
| (Component A) | |
| Olive oil | 10.0 |
| Isopropyl myristate | 1.0 |

-continued

| Ingredients | Mixing ratio (mass %) |
|---|---|
| Polyoxyethylene (6) nonylphenyl ether | 0.5 |
| Propylene glycol | 1.0 |
| Glycerin | 2.0 |
| (Component B) | |
| Methylparaben | 0.1 |
| Ethanol | 7.0 |
| Purified water | Balance to the total of 100 |
| (Component C) | |
| Bis (diethylene glycol monoethyl ether) fumarate | 0.0001 |

(2) Preparation Method

Bis(diethylene glycol monoethyl ether)fumarate as Component C was added to Component B. After dissolving Components A and B homogeneously, Components A and B were mixed and dispersed with stirring to prepare a lotion. The lotion prepared was poured in a container. The content was shaken to effect a uniform dispersion before use.

Application Example 3

Bath Agent

A bath agent with the following composition was prepared by a common method.

| Ingredients | Mixing ratio (mass %) |
|---|---|
| Bis (diethylene glyol monoethyl ether) fumarate | 1.0 |
| Sodium hydrogen carbonate | Balance |
| Sodium carbonate | 20.0 |
| Sodium sulfate | 15.0 |
| Sodium chloride | 7.5 |
| Silica | 0.5 |
| 1,3-butylene glycol | 1.0 |
| Urea | 1.0 |
| Seaweed extract | 1.0 |
| Colorant | Appropriate amount |
| Dextrin | Appropriate amount |
| Perfume | Appropriate amount |

Application Example 4

Skin Cream

A skin cream was prepared by mixing the fumaric acid diester derivative and retinoic acid according to the following composition.

| Ingredients | Mixing ratio (mass %) |
|---|---|
| (Component A) | |
| Beeswax | 2.0 |
| Stearic acid | 5.0 |
| Stearyl alcohol | 5.0 |
| Hydrogenated lanolin | 2.0 |

-continued

| Ingredients | Mixing ratio (mass %) |
|---|---|
| Squalene | 20.0 |
| Sorbitan monostearate | 3.0 |
| Polyoxyethylene (20) sorbitan monostearate | 3.0 |
| Propylene glycol | 5.0 |
| (Component B) | |
| Methylparaben | 0.2 |
| Purified water | Balance to the total of 100 |
| (Component C) | |
| Bis (diethylene glycol monoethyl ether) fumarate | 10.0 |
| Retinoic acid | 1.0 |

(2) Preparation Method

Bis(diethylene glycol monoethyl ether)fumarate and retinoic acid as Component C were added to Component B. After dissolving Components A and B separately by heating to 80° C., both components were combined and then cooled to 30° C. with stirring to make a skin cream.

Application Example 5

Skin Lotion

A skin lotion was prepared by mixing the fumaric acid diester derivative and retinoic acid according to the following composition.

(1) Composition of a Skin Lotion

| Ingredients | Mixing ratio (mass %) |
|---|---|
| (Component A) | |
| Olive oil | 10.0 |
| Isopropyl myristate | 1.0 |
| Polyoxyethylene (6) nonylphenyl ether | 0.5 |
| Propylene glycol | 1.0 |
| Glycerin | 2.0 |
| (Component B) | |
| Methylparaben | 0.1 |
| Ethanol | 7.0 |
| Purified water | Balance to the total of 100 |
| (Component C) | |
| Bis (diethylene glycol monoethyl ether) fumarate | 0.0001 |
| Retinoic acid | 1.0 |

(2) Preparation Method

Bis(diethylene glycol monoethyl ether)fumarate and retinoic acid as Component C were added to Component B. After dissolving Components A and B homogeneously, Components A and B were mixed and dispersed with stirring to prepare a lotion. The lotion prepared was filled in a container. The contents were shaken to effect uniform dispersion before use.

Application Example 6

Skin Lotion

A skin lotion was prepared by mixing the fumaric acid diester derivative and retinoic acid according to the following composition.

(1) Composition of a Skin Lotion

| Ingredients | Mixing ratio (mass %) |
|---|---|
| (Component A) | |
| Olive oil | 10.0 |
| Retinyl acetate | 0.02 |
| Isopropyl myristate | 1.0 |
| Polyoxyethylene (6) nonylphenyl ether | 0.5 |
| Propylene glycol | 1.0 |
| Glycerin | 2.0 |
| (Component B) | |
| Methylparaben | 0.1 |
| Ethanol | 7.0 |
| Purified water | Balance to the total of 100 |
| (Component C) | |
| Bis (diethylene glycol monoethyl ether) fumarate | 3.0 |
| Retinoic acid | 1.0 |

(2) Preparation Method

Bis(diethylene glycol monoethyl ether)fumarate and retinoic acid as Component C were added to Component B. After dissolving Components A and B homogeneously, Components A and B were mixed and dispersed with stirring to prepare a lotion. The lotion prepared was filled in a container. The contents were shaken to effect uniform dispersion before use.

Application Examples 7 through 9

Skin Cream

Skin cream was prepared according to the following composition in a conventional method.

| Ingredients | Application Example 7 | Application Example 8 | Application Example 9 |
|---|---|---|---|
| | Mixing ratio (mass %) | | |
| Bis (diethylene glycol monoethyl ether) fumarate | 0.1 | 0.1 | 0.1 |
| Stearic acid | 1 | 1 | — |
| Isostearic acid | — | — | 1 |
| Glycerin monostearate | 2 | 2 | 2 |
| Behenyl alcohol | 2 | 2 | 2 |
| Bleached beeswax | 1 | 1 | — |
| Cetyl myristate | 1 | 1 | 1 |
| Sorbitan sesquioleate | 1 | 1 | 1 |
| N-stearoylphytosphyngosine | 0.1 | 0.1 | 0.1 |
| Hydrogenated lecithin | 0.1 | 0.1 | 0.1 |
| Vegetable squalane | 5 | 5 | 5 |
| Retinyl palmitate | 0.05 | — | — |

-continued

| Ingredients | Application Example 7 | Application Example 8 | Application Example 9 |
|---|---|---|---|
| | Mixing ratio (mass %) | | |
| Octyldodecyl myristate | 5 | 5 | 5 |
| *Phellodendron* bark extract | 0.1 | 1 | 0.1 |
| *Pyracantha fortuneana* extarct | 0.1 | 0.3 | — |
| Water-soluble *glycyrrhiza* extract | — | — | 0.1 |
| 1,3-butylene glycol | 5 | 10 | 5 |
| Conc. Glycerin | 5 | 5 | 5 |
| Parahydroxybenzoate ester | 0.2 | 0.2 | 0.2 |
| N-acetylglucosamine oligomer | 0.1 | 0.1 | 0.1 |
| Magnesiumascorbylphosphate | 0.1 | 0.1 | 0.1 |
| Sodium ascorbylphosphate | 0.1 | 0.1 | 0.1 |
| Gamma-aminobutyric acid | 0.1 | 0.1 | 0.1 |
| Sodium N-stearoylglutamate | 0.2 | 0.2 | 0.2 |
| Alkyl-modified carboxyvinyl polymer*[1] | 0.05 | 0.05 | 0.05 |
| Nicotinamide | 0.1 | 0.1 | 0.1 |
| Sarcosine | 0.1 | 0.1 | 0.1 |
| Purified water | Balance | Balance | Balance |

*[1]PEMULEN ™ TR-1, ex B F. Goodrich Company

Application Examples 10 and 11

Lotion

Lotions were prepared according to the following composition in a conventional method.

| Ingredients | Application Example 10 | Application Example 11 |
|---|---|---|
| | Mixing ratio (mass %) | |
| Bis (diethylene glycol monoethyl ether) fumarate | 0.1 | 0.1 |
| *Phellodendron* bark extract | 0.1 | 0.3 |
| *Hibiscus* extract | 0.2 | 0.5 |
| Lactic acid bacteria fermentation solution | 0.1 | 0.1 |
| 1,3-butylene glycol | 5 | 5 |
| Dipropylene glycol | — | 5 |
| Raffinose | 1 | 1 |
| Ethanol | — | 1 |
| Phenoxyethanol | 0.2 | 0.2 |
| Pectin | — | 0.05 |
| Xanthan gum | — | 0.1 |
| Sodium citrate | 0.05 | 0.05 |
| Horsetail extract | 0.1 | 0.1 |
| Diisopropylamine dichloroacetate | 0.2 | 0.2 |
| Gamma-amino-beta-hydroxybutylic acid | 0.2 | 0.2 |
| Sodium hyaluronate | 0.001 | 0.001 |
| Dipotassium glycyrrhizinate | 0.2 | 0.2 |
| *Naematoloma sublateritum* extract | 0.05 | 0.05 |
| Decarboxy carnosine hydrochloride | 0.05 | 0.05 |
| Perfume | 0.02 | 0.02 |
| Purified water | Balance | Balance |

Application Examples 12 through 14

Gel

Gels were prepared according to the following composition in a conventional method.

|                                    | Mixing ratio (mass %) | | |
|---|---|---|---|
| Ingredients | Application Example 12 | Application Example 13 | Application Example 14 |
| Bis (diethylene glycol monoethyl ether) fumarate | 0.1 | 0.1 | 0.1 |
| Decamethylcyclo-pentasiloxane | 10 | 10 | 10 |
| Isostearyl isostearate | 1 | — | — |
| Olive oil | — | 1 | — |
| Macadamianut oil | — | — | 1 |
| *Eucalyptus* oil | 0.1 | — | 0.1 |
| Hexyldecanol | 1 | 0.1 | — |
| dl-alpha-tocopheryl nicotinate | — | 0.1 | — |
| Retinol | 0.1 | — | — |
| Polyoxyethylene (60) hydrogenated castor oil | 2 | 2 | 2 |
| Spherical silicone powder*[2] | 1 | 1 | 5 |
| *Phellodendron* bark extract | 0.1 | 1 | 0.1 |
| Water-soluble chlorophyll | 0.02 | 0.02 | 0.02 |
| *Salvia* extract | — | 0.3 | 0.1 |
| 1,3-butylene glycol | 5 | 10 | 5 |
| Sorbitol solution | 3 | 3 | 3 |
| Polyethylene glycol 4000 | 1 | 1 | 1 |
| Carboxyvinyl polymer | 0.2 | 0.2 | 0.2 |
| Glycoceramide*[3] | 0.1 | 0.1 | 0.1 |
| Parahydroxybenzoate ester | 0.2 | 0.2 | 0.2 |
| Mevalonolactone | 0.5 | 0.5 | 0.5 |
| Edetic acid salt | 0.02 | 0.02 | 0.02 |
| Potassium hydroxide | 0.05 | 0.05 | 0.05 |
| Purified water | Balance | Balance | Balance |

*[2]Tospearl ™, ex GE Toshiba Silicone Corp.
*[3]Bioceramide ™, ex Kibun Food Chemical Corp.

Application Examples 15 through 17

Lipophilic Cream

Lipophilic creams were prepared according to the following composition in a conventional method.

|                                    | Mixing ratio (mass %) | | |
|---|---|---|---|
| Ingredients | Application Example 15 | Application Example 16 | Application Example 17 |
| Bis(diethylene glycol monoethyl ether)fumarate | 0.1 | 0.1 | 0.1 |
| Comodified silicone*[4] | 2 | 2 | 2 |
| Polyoxyethylene modified silicone dispersion*[5] | — | 2 | — |
| Squalane | — | — | 10 |
| Decamethylcyclo-pentasiloxane | 15 | 20 | 10 |
| Retinol | 0.05 | 0.05 | 0.05 |
| Methylpolysiloxane | 5 | 2 | 3 |
| Cholesteryl long-chain branched fatty acids ester*[6] | — | — | 3 |
| Silicone elastomer dispersion*[7] | 5 | 2 | — |
| *Phellodendron* bark extract | 1 | 1 | 1 |
| *Glycyrrhiza* extract | 0.1 | 0.1 | 0.1 |
| Water-soluble chlorophyll | 0.02 | 0.02 | 0.02 |
| Sodium chloride | 1 | 1 | 1 |
| Dipropylene glycol | 5 | 5 | 5 |
| Conc. Glycerin | 5 | 5 | 5 |
| Raffinose | 1 | 1 | 1 |
| Parahydroxybenzoate ester | 0.3 | 0.3 | 0.3 |
| N-methyl-L-serine | 0.5 | 0.5 | 0.5 |
| Purified water | Balance | Balance | Balanced |

*[4]ABIL ™ EM 90, ex Goldschmidt AG.
*[5]Silicone BY22-008, ex Toray Dow Corning Silicone Co.
*[6]YOFCO CLE-NH, ex Nippon Seika Corporation Co.
*[7]Trefil ™, ex Toray Dow Corning Silicone Co.

Application Examples 18 through 20

Sunscreen

Sunscreens were prepared according to the following composition in a conventional method.

|                                    | Mixing ratio (mass %) | | |
|---|---|---|---|
| Ingredients | Application Example 19 | Application Example 20 | Application Example 21 |
| Bis(diethylene glycol monoethyl ether)fumarate | 0.1 | 0.1 | 0.1 |
| Dioctyl ether | 22 | 15 | 10 |
| Comodified silicone*[4] | 2 | 2 | 2 |
| Glyceryl tri-2-ethylhexanoate | — | — | 5 |
| Hydrogenated oil | — | — | 0.1 |
| Methylphenyl polysiloxane | — | 3 | — |
| Macadamianut fatty acid phytosteryl ester | — | — | 2 |
| 2-ethylhexyl 4-methoxycinnamate | — | 7 | 7 |
| Titanium oxide | 5 | — | 4 |
| Zinc oxide | 5 | — | 4 |
| *Phellodendron* bark extract | 1 | 1 | 1 |
| Magnesium chloride | 1 | 1 | 1 |
| 1,3-butylene glycol | 5 | 5 | 5 |
| Phenoxyethanol | 0.3 | 0.3 | 0.3 |
| *Hibiscus* extract | 1 | 1 | 1 |
| *Aloe* extract | 0.1 | 0.1 | 0.1 |
| Yeast extract*[8] | 1 | 1 | 1 |
| Purified water | Balance | Balance | Balance |

*[4]ABIL ™ EM90, ex Goldschmidt AG.
*[8]DISMUTIN ™, ex Pentapharm AG.

INDUSTRIAL APPLICABILITY

The present invention provides an epidermal barrier function-enhancing agent and a composition for skin external application which are very safe, quickly ameliorate the epidermal permeability barrier function disruption, and have excellent effects on maintaining the skin in a cosmetologically healthy state; a HB-EGF expression-inducing agent to enhance epidermal turnover; an amphiregulin expression inhibitor to diminish epidermal hyperproliferation; an agent to be used together with retinoic acid or a derivative thereof to prevent dry skin caused by retinoic acid or a derivative thereof; and an ameliorating agent for aged skin which ameliorates metabolic disruption and skin thinning of the skin due to aging.

We claim:

1. A method for enhancing epidermal permeability barrier function of skin, comprising the step of externally administering to the skin an external composition comprising a fumaric acid diester derivative expressed by the following general formula (1) as an active ingredient:

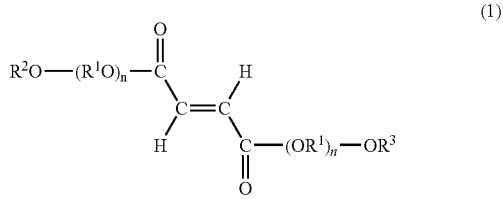

wherein $R^1$ represents a $C_{1-4}$ alkylene group; $R^2$ and $R^3$ each represents a linear or branched $C_{1-8}$ alkyl group; and n is an integer of 2 to 5; and said fumaric acid diester derivative is administered in an amount of 0.001 to 15.0 mass % relative to a total amount of the composition.

2. The method for enhancing epidermal permeability barrier function of skin according to claim 1, wherein the administered amount of the fumaric acid diester derivative of formula (1) inhibits excessive epidermal proliferation.

3. The method for enhancing epidermal permeability barrier function of skin according to claim 1, wherein the administered amount of the fumaric acid diester derivative of formula (1) inhibits expression of amphiregulin.

4. The method for enhancing epidermal permeability barrier function of skin according to claim 1, wherein the administered amount of the fumaric acid diester derivative of formula (1) induces expression of heparin-binding epidermal growth factor-like growth factor (HB-EGF).

* * * * *